United States Patent
Morris et al.

[11] Patent Number: 5,968,085
[45] Date of Patent: Oct. 19, 1999

[54] PACING LEAD WITH INTEGRAL GUIDANCE USING ULTRASOUND

[75] Inventors: Mary M. Morris, Mounds View; David Lipson, Shoreview, both of Minn.

[73] Assignee: Medtronic, Inc., Minneapolis, Mich.

[21] Appl. No.: 09/063,170

[22] Filed: Apr. 20, 1998

[51] Int. Cl.$^6$ ............................................ A61N 1/05
[52] U.S. Cl. ................................................. 607/116
[58] Field of Search ......................... 607/116, 119, 607/122

[56] References Cited

U.S. PATENT DOCUMENTS

| | | |
|---|---|---|
| 4,217,913 | 8/1980 | Dutcher . |
| 4,570,642 | 2/1986 | Kane et al. . |
| 4,697,595 | 10/1987 | Breyer et al. . |
| 5,161,536 | 11/1992 | Vilkomerson et al. . |
| 5,343,865 | 9/1994 | Gardineer et al. . |
| 5,421,336 | 6/1995 | DeBernardis . |

*Primary Examiner*—William E. Kamm
*Attorney, Agent, or Firm*—Reed A. Duthler; Harold R. Patton

[57] ABSTRACT

A pacing lead of the type having a hollow lead body with a conductor linking the electrode at one end with the connector at the other end has a guide wire or stylet either connected to a mechanical vibrator or carrying an ultrasonic transducer in order to cause the guidewire to move within the body to facilitate the display of the catheter position on external ultrasonic monitoring equipment.

5 Claims, 9 Drawing Sheets

PACING LEAD WITH INTEGRAL GUIDANCE USING ULTRASOUND

BACKGROUND OF THE INVENTION

The present invention relates to visualization of medical devices within the human body generally and more particularly to visualization of implantable cardiac pacing and defibrillation leads by means of ultrasound.

Cardiac pacing and defibrillation leads are generally put in under fluoroscopic observation, allowing the physician to follow the course of the lead as it is passed through the venous system into the heart. However, as fluoroscopes are extremely expensive, a less costly method of visualization of cardiac pacing and defibrillation leads would be desirable. One alternative mechanism for visualization of devices placed within the body is by means of ultrasound. In U.S. Pat. No. 5,421,336 issued to DeBernardis, incorporated herein by reference in its entirety, the use of a vibrator coupled to an interventional device to enhance its visibility in an ultrasound scan is disclosed. In particular, the vibrator member induces three-dimensional flexural waves which propagate along the member, causing it to light up on the display of the ultrasound scan. The DeBernardis patent also discloses attaching a vibrator to a member such as a guidewire or stylet inserted into a tubular probe, to localize the probe. A second method of visualizing a catheter or pacing lead is to place an ultrasound sensor on or in the lead body and employ the sensor in conjunction with an ultrasound imaging system to localize the sensor in the ultrasound scan. Examples of such localization systems are disclosed in U.S. Pat. No. 5,161,536 issued to Vilkomerson et al and in U.S. Pat. No. 4,697,595 issued to Breyer et al., both incorporated herein by reference in their entireties.

SUMMARY OF THE INVENTION

The present invention is directed to an improved cardiac pacing or defibrillation lead optimized for use in conjunction with a stylet or guidewire in conjunction with a vibrator or for use in conjunction with a stylet or guidewire carrying an ultrasound transducer. The present invention accomplishes this enhanced visibility in some embodiments by providing an aperture located at or adjacent the distal end of the lead, through which the vibrating tip of the associated guidewire or stylet or through which the ultrasound sensor may be coupled to the surrounding medium, typically blood. In a first group of embodiments according to the present invention, the vibrating member or the device carrying the transducer is a stylet which is used to guide the lead to its desired location within the heart, while coupled to a vibrator. In some embodiments within this first group, the distal end of the lead, typically the body of the electrode located at the distal end of the lead, is provided with an aperture through which the distal end of the stylet may not pass. The distal end of the stylet may thus be employed to push or guide the lead to its desired location while acoustically coupled to the medium surrounding the lead body by means of the aperture. In other embodiments in this first group, the stylet is coupled mechanically to the surrounding body fluid by means of the electrode itself. A second group of embodiments of the present invention is intended to be employed in conjunction with a guidewire coupled to a vibrator or carrying an ultrasound transducer. In this second group of embodiments, the lead is provided with an aperture at the distal end of the lead through which the guidewire may pass. The guidewire is located at the desired position within the heart while coupled to the vibrator or while the sensor receives signals from an external ultrasound scanner, and the lead is subsequently advanced along the guidewire to the desired location.

DETAILED DESCRIPTION OF THE PREFERRED EMBODIMENTS

Figure 1:
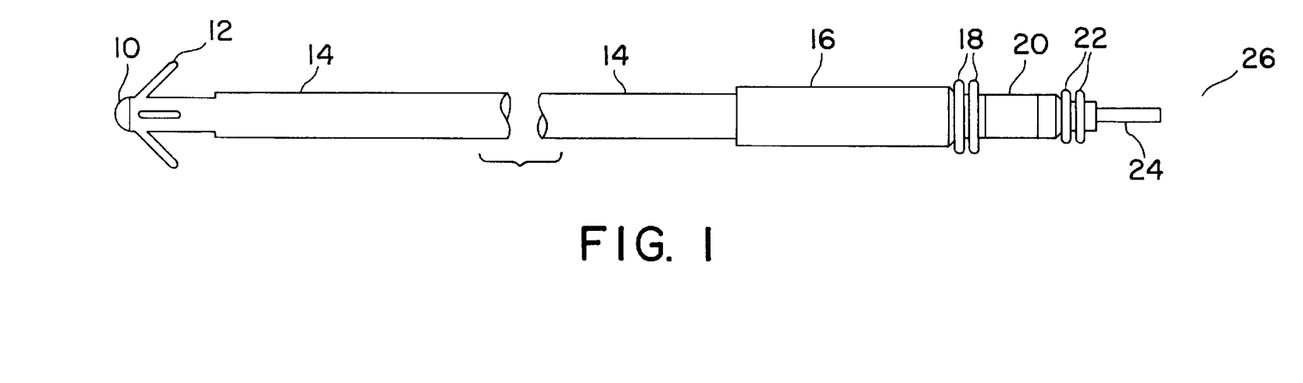
FIG. 1 is a plan view of a lead in which the present invention is practiced in conjunction with a vibrating stylet or guidewire.

FIG. 1 is a plan view illustrating the general configuration of a cardiac pacing lead according to the present invention. The lead is provided with a pacing electrode 10 at its distal tip, and associated tines 12 which assist in maintaining the lead in its desired position within the heart. Electrode 10 and tines 12 are mounted at the distal portion of an elongated insulative lead body 14 which terminates at its proximal end in an electrical connector assembly 16. Connector assembly 16 carries a connector pin 24 and a connector ring 20 in conjunction with sealing rings 18 and 22. Connector assembly 16 as illustrated corresponds to an IS-1 standard electrical connector. In the embodiment illustrated, connector pin 24 is coupled to electrode 10, while connector ring 20 is unused. In other embodiments, connector ring 20 might be coupled to an additional cardiac pacing electrode, a defibrillation electrode or a sensor. Emerging from connector pin 24 is the handle 26 of a stylet inserted through connector pin 24, used to advance the lead to its desired location within the heart in a conventional manner. The structure of the lead as illustrated corresponds to a conventional cardiac pacing or defibrillation electrode with the exception of the structure of the distal portion of the lead as illustrated in more detail in FIGS. 3 through 6 below.

Figure 2:
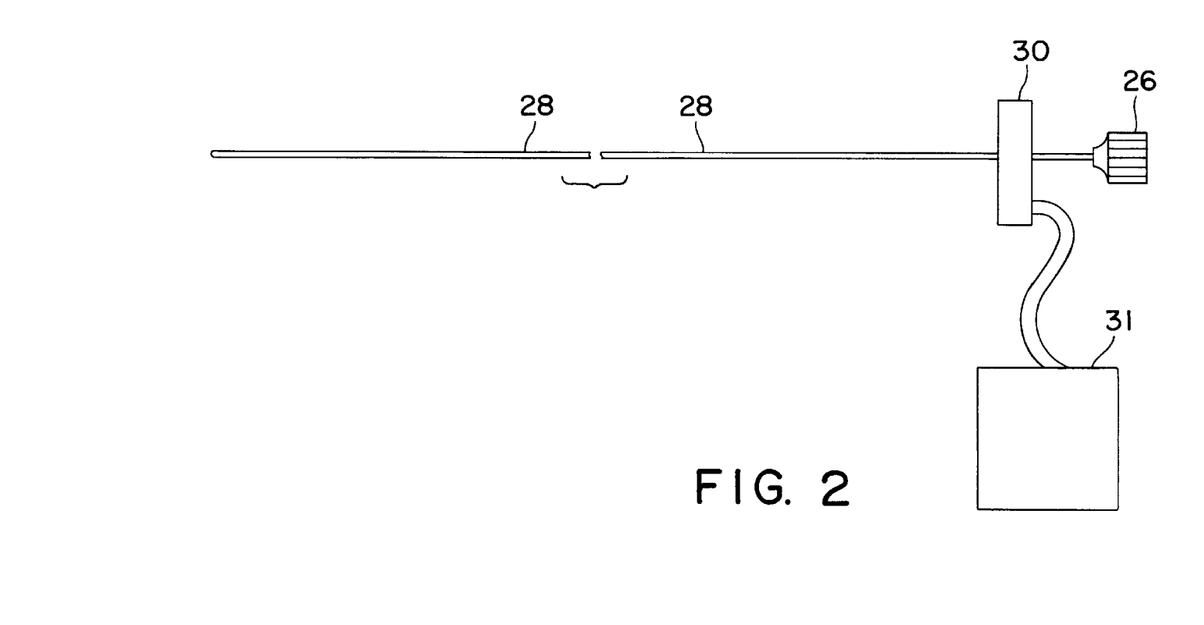
FIG. 2 is a plan view of a stylet coupled to a vibrator, employed to assist in visualizing the location of the lead of FIG. 1.

FIG. 2 is a plan view of a stylet 26 corresponding to the stylet inserted in the lead in FIG. 1, in conjunction with a vibrator 30. Knob 26 is visible at the proximal end of the stylet. Vibrator 30 is coupled to a source of ultrasound energy 31. Vibrator 30 may correspond to that disclosed in U.S. Pat. No. 5,421,336 issued to DeBernardis. The source of ultrasound energy 31 may correspond to that disclosed in U.S. Pat. No. 5,343,865 issued to Gardineer et al. and incorporated herein by reference in its entirety. When activated, vibrator 30 induces three-dimensional flexural oscillations which propagate down stylet 28 causing it to become illuminated in the display of an ultrasound scan through which the stylet passes. Vibrator 30 may also be used to vibrate a guidewire, as discussed below.

Figure 3:
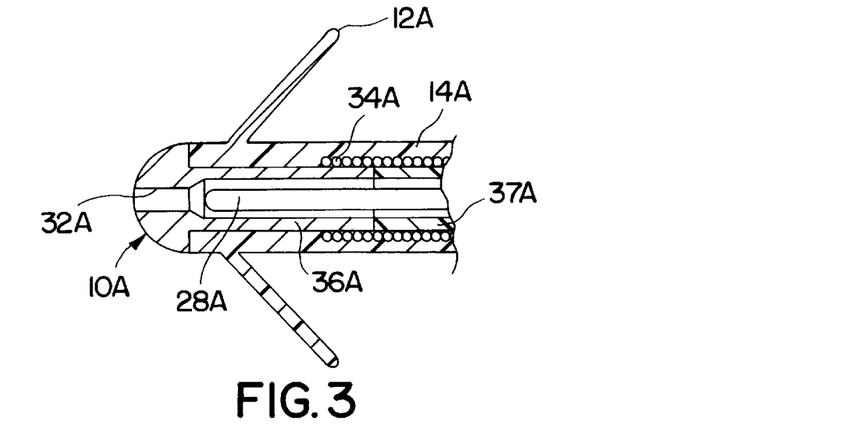
FIGS. 3, 4, 5 and 6 are cross-sectional views through the distal portions of leads according to the first group of embodiments of the present invention which employ a vibrating stylet.

FIG. 3 is a sectional view through the distal portion of the first embodiment of the lead according to the first group of embodiments in the present invention. An electrode 10A is mounted to the distal end of the insulated lead body 14A, which also carries pliant times 12A. The distal portion of 10A is provided with a bore 32A open to the interior lumen within shank 36A of the electrode. The diameter of bore 32A is less than the outer diameter of the distal portion of stylet 28A so that the distal tip of stylet 28A may bear against the interior of electrode 10A and may be employed to advance the lead through the vascular system. Electrode shank 36A is coupled to a connector pin at the proximal end of the lead by means of coiled conductor 34A which may be welded or otherwise attached to electrode shank 36A. An optional insulative sleeve 37A is provided internal to conductor 34A.

Figure 4:
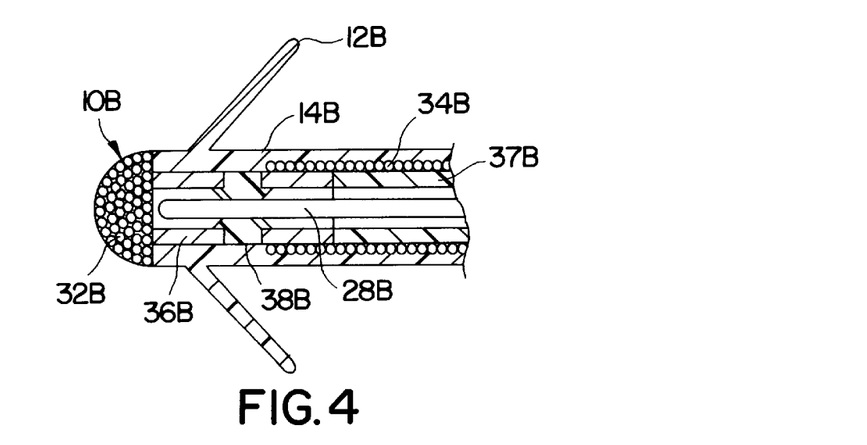

FIG. 4 illustrates a second embodiment of a lead according to the first group of embodiments of the present invention. In the lead illustrated in FIG. 4, insulative lead body 14B carries at its distal end an electrode 10B and pliant tines 12B. Electrode 10B takes the form of a porous sintered body 32B coupled to a conductive electrode shank 36B. Electrode 32B is fabricated so that fluid may flow through porous section 32B into the interior lumen of electrode shank 36B. The porosity of porous section 32B is such that the distal end of stylet 28B may not pass therethrough, so that the stylet 22B may be employed to advance the lead through the vascular system. In this embodiment of the invention, a circumferential seal 38B is provided to prevent propagation of fluid proximally up the lead body from the distal portion of the lumen within connector shank 36B. Also provided is an optional internal insulative sleeve 37B.

Figure 5:
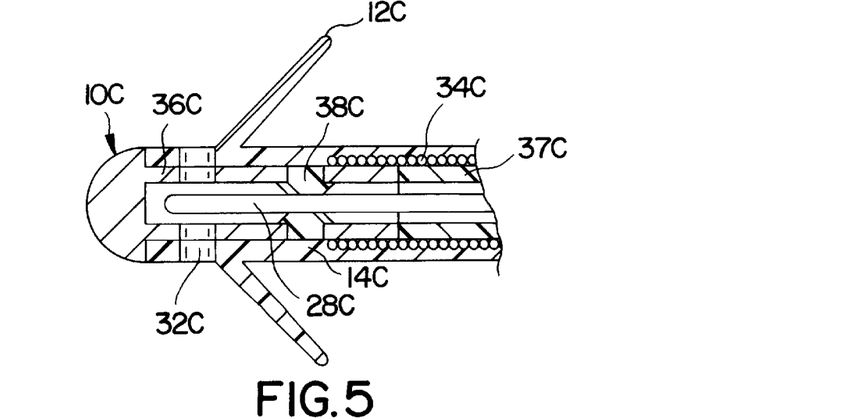

FIG. 5 illustrates a third sectional view through the distal end of a third alternative embodiment of a lead according to the first group of embodiments of the present invention. In this embodiment of the invention, the insulative lead body 32C carries an electrode 10C at its distal end, and associated pliant tines 12C. Electrode 10C has a closed electrode tip extending from a tubular conductive electrode shank 36C. Electrode shank 36C and insulative lead body 34C are provided with aligned apertures providing for side ports 32C coupling the interior of the lumen within shank 36C to the exterior of the lead. Because the lumen within the electrode 10C is closed ended, stylet 28C may be employed to bear against the interior of the electrode and to advance the lead to its desired location within the heart. Also visible are an optional circumferential seal 38C and optional internal insulative sleeve 37C. Conductor 34C couples electrode shank 36C to a connector pin located at the proximal end of the lead.

Figure 6:
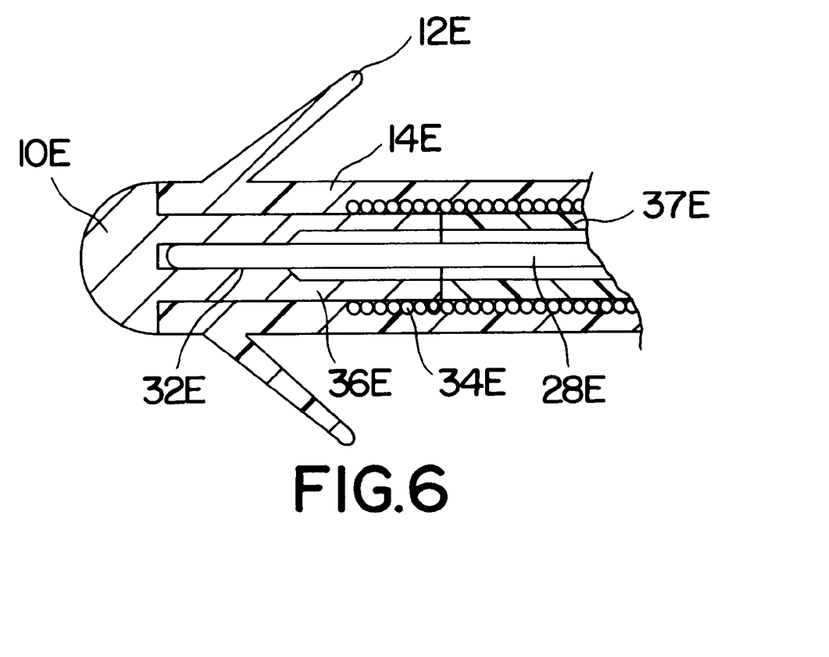

FIG. 6 is a sectional view through the distal portion of a fourth embodiment of the lead according to the first group of embodiments in the present invention. An electrode 10E is mounted to the distal end of the insulated lead body 14A, which also carries pliant times 12E. The distal portion of 10E is provided with a reduced diameter bore 32E which mechanically engages the distal end of stylet 28E, coupling them together so that the vibrations of the stylet 28E are coupled to the surrounding body fluid via the Electrode 10E. As in the above-illustrated embodiments, the distal tip of stylet 28E may bear against the interior of electrode 10E and may be employed to advance the lead through the vascular system. Electrode shank 36E is coupled to a connector pin at the proximal end of the lead by means of coiled conductor 34E which may be welded or otherwise attached to electrode shank 36E. An optional insulative sleeve 37E is provided internal to conductor 34E.

In all of the embodiments of FIGS. 3–7, it is desirable that adequate clearance be provided between the interior of the lead body and the connector pin through which the stylet or guidewire is introduced and the stylet or guidewire itself. This assures that vibrations applied to the proximal end of the stylet may be efficiently propagated to its distal tip rather than being damped out by close contact with the interior of the lead body.

Figure 7:
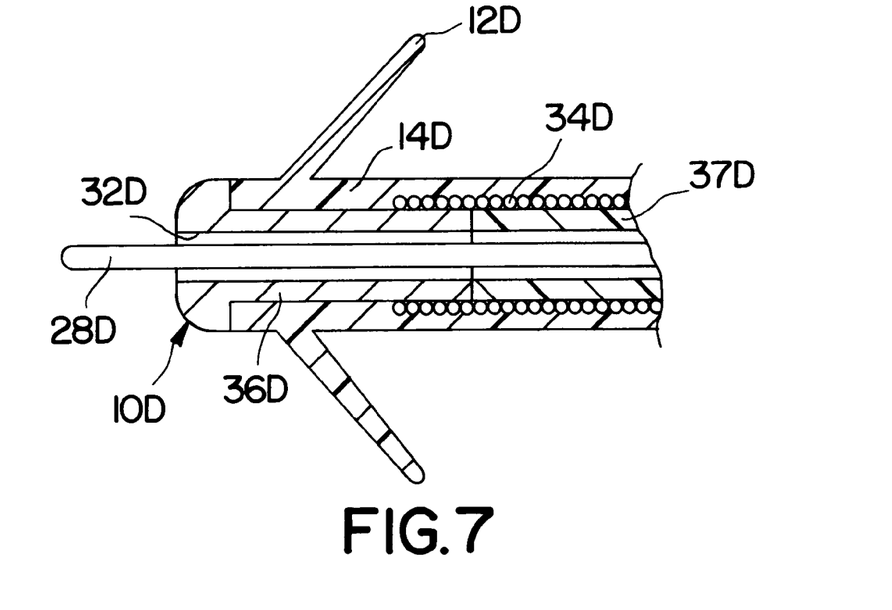
FIG. 7 is a cross-sectional view of a lead according to the second group of embodiments of the present invention employing a vibrating guidewire.

FIG. 7 illustrates a sectional view through the distal end of a lead according to the second group of embodiments of the present invention. In this embodiment, insulative body 34D carries an electrode 32B at its distal end, along with pliant tines 112D. In this embodiment, electrode 32D takes the form of an electrode having an aperture 32D open to the interior lumen within conductive shank 36D, through which guidewire 28D may freely pass. In use, guidewire 28D is advanced first to the desired location for electrode 10D, and then the lead is subsequently advanced along guidewire 28D to the desired location. Also visible in this view is an optional internal insulative sleeve 37D.

In all of the embodiments of FIGS. 3–7, it is desirable that adequate clearance be provided between the interior of the lead body and the connector pin through which the stylet or guidewire is introduced and the stylet or guidewire itself. This assures that vibrations applied to the proximal end of the stylet may be efficiently propagated to its distal tip rather than being damped out by close contact with the interior of the lead body .

Figure 8:
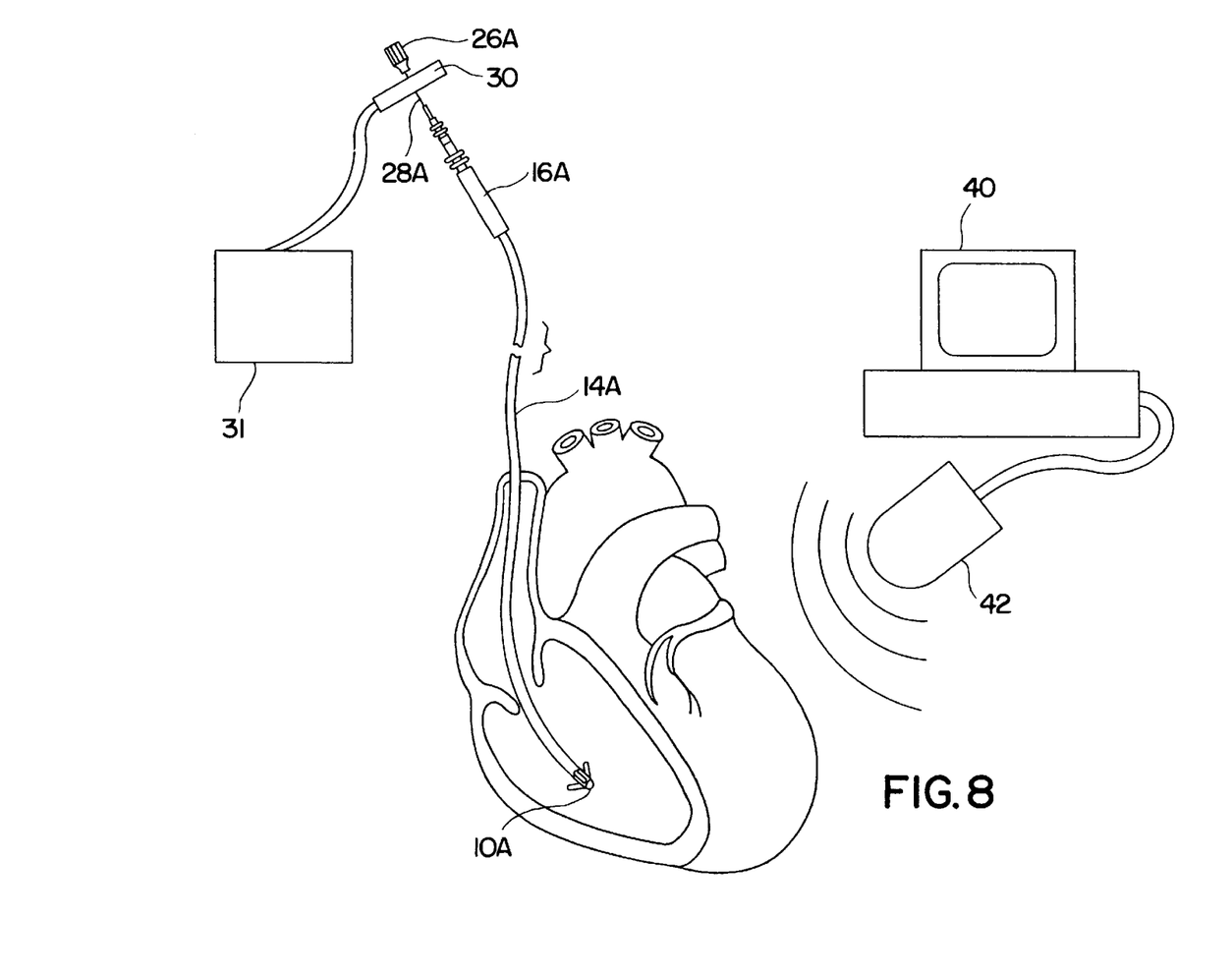
FIG. 8 illustrates the use of a lead according to the first group of embodiments of the present invention, using a vibrating stylet.

FIG. 8 illustrates the method of use of leads according to the first group of embodiments of the present invention. The lead body 14A is advanced through the vascular system into the ventricle by means of stylet 28A, shown extending from connector assembly 16A and stylet knob 26A. When activated by ultrasound source 31, vibrator 30 causes stylet 28A to be illuminated where it passes through the ultrasound scan of ultrasound scan of ultrasound scanner 42, rendering it visible on ultrasound display 40.

Figure 9:
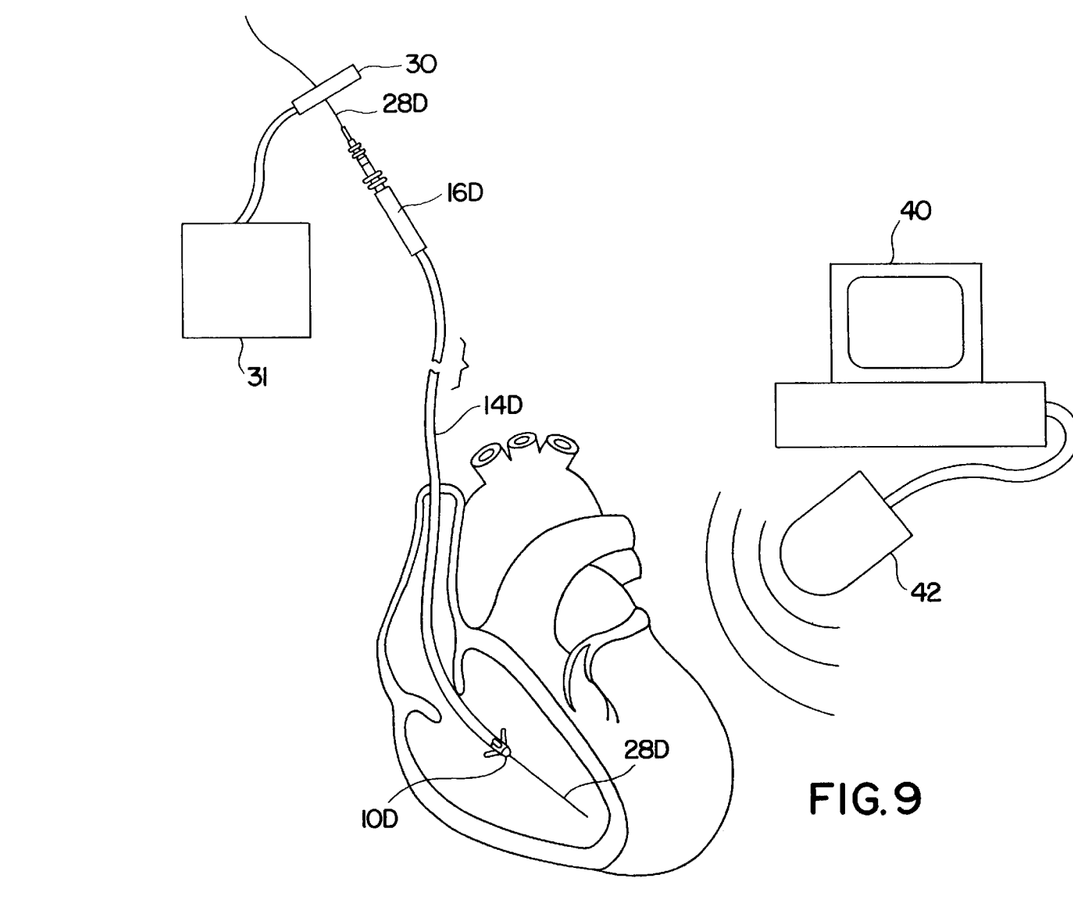
FIG. 9 illustrates the use of a lead according to the second group of embodiments of the present invention, using a vibrating guidewire.

FIG. 9 illustrates the method of use of leads according to the second group of embodiments of the present invention. In this embodiment, the guidewire 28D is first passed to a desired location within the heart and lead body 14D is thereafter slid along guidewire 28D to the desired location. Guidewire 28D is coupled to vibrator 30, at a point proximal to the point it emerges from connector assembly 16B, at a point proximal to the point it emerges from connector assembly 16D. When activated by ultrasound source 31, vibrator 30 causes flexural waves to propagate down guidewire 28, illuminating it where it passes through the scan of ultrasound scanner 42, rendering it visible on ultrasound display 40.

Figure 10:
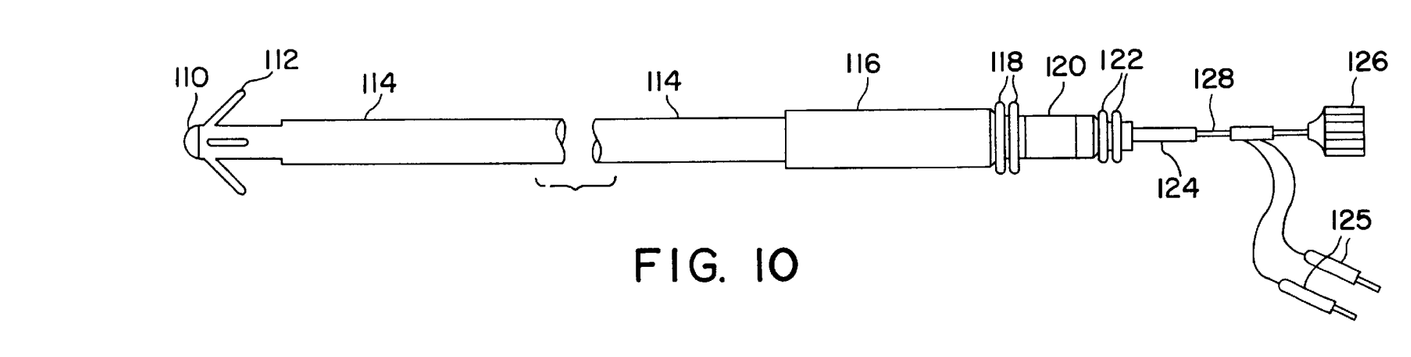
FIG. 10 is a plan view of a lead in which the present invention is practiced in conjunction with a stylet or guidewire carrying an ultrasound transducer.

FIG. 10 is a plan view illustrating the general configuration of a cardiac pacing lead according to the present invention for use in conjunction with a stylet or guidewire carrying an ultrasound transducer. The lead is provided with a pacing electrode 10 at its distal tip, and associated tines 112 which assist in maintaining the lead in its desired position within the heart. Electrode 110 and tines 112 are mounted at the distal portion of an elongated insulative lead body 114 which terminates at its proximal end in an electrical connector assembly 16. Electrical connector assembly 116 carries a connector pin 124 and a connector ring 120 in conjunction with sealing rings 118 and 122. Connector assembly 116 as illustrated corresponds to an IS-1 standard electrical connector. In the embodiment illustrated, connector pin 124 is coupled to electrode 110, while connector ring 120 is unused. In other embodiments, connector ring 120 might be coupled to an additional cardiac pacing electrode, a defibrillation electrode or a sensor. Emerging from connector pin 124 is the handle 126 of a stylet 128 used to advance the lead to its desired location within the heart in a conventional manner. Electrical connectors 125 serve to couple the ultrasound transducer located on the stylet to associated processing circuitry. The structure of the lead as illustrated corresponds to a conventional cardiac pacing or defibrillation electrode with the exception of the structure of the distal portion of the lead as illustrated in more detail in FIGS. 12 and 13, discussed below.

Figure 11:
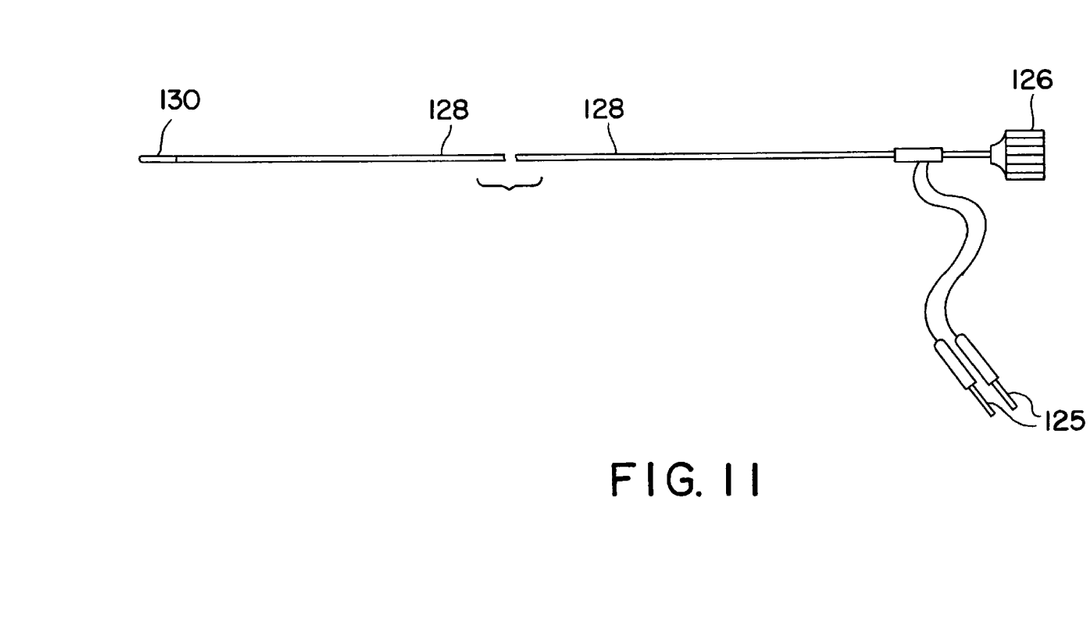
FIG. 11 is a plan view of a stylet coupled carrying an ultrasound transducer, employed to assist in visualizing the location of the lead of FIG. 1.

FIG. 11 is a plan view of a stylet 128 corresponding to the stylet inserted in the lead in FIG. 10, carrying at its distal end an ultrasound transducer 130. Knob 126 is visible at the proximal end of the stylet. Electrical connectors 125 serve to couple the ultrasound transducer 130 to associated processing circuitry as described in the above-cited Vilkomerson et al. patent. Stylet 128 may be replaced with a guidewire, carrying a corresponding ultrasound transducer, in conjunction with lead according to the second group of embodiments discussed herein.

Figure 12:
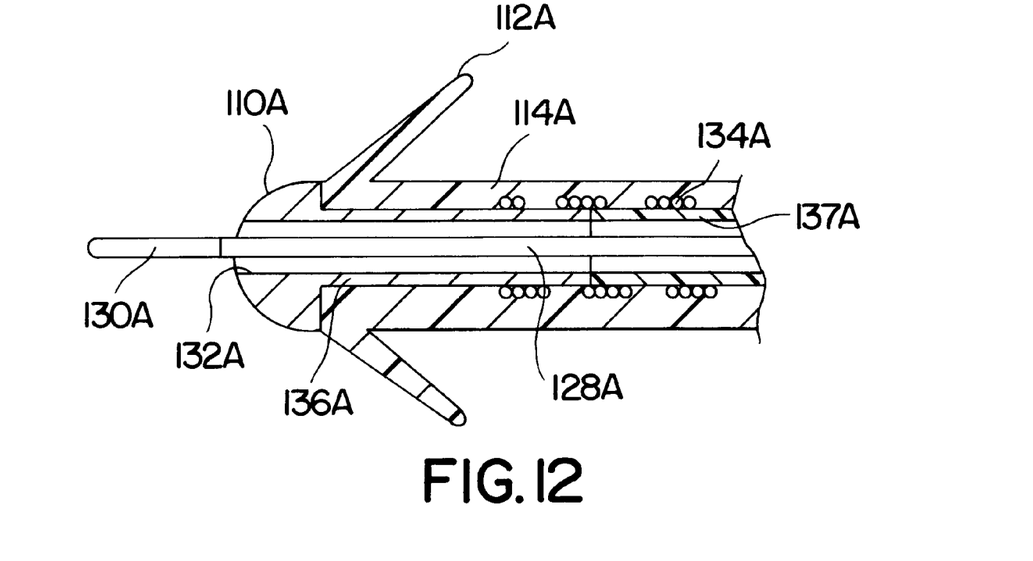
FIG. 12 is a cross-sectional view through the distal portion of a lead according to the first group of embodiments of the present invention which employs a stylet carrying an ultrasound transducer

FIG. 12 is a sectional view through the distal portion of a second embodiment of a lead according to the second group of embodiments in the present invention, employing a guidewire carrying an ultrasound transducer. An electrode 110A is mounted to the distal end of the insulated lead body 114A, which also carries pliant times 112A. The distal portion of electrode 110A is provided with a bore 132A open to the interior lumen within shank 136A of the electrode. The diameter of bore 132A is greater than the outer diameter of the distal portion of guidewire 128A so that the distal tip of guidewire 128A carrying ultrasound transducer 130a may exit the distal end of electrode 110A as illustrated, so that the lead may be advanced along guidewire 128A. Electrode shank 136A is coupled to a connector pin at the proximal end of the lead by means of coiled conductor 134A which may be welded or otherwise attached to electrode shank 136A. An optional insulative sleeve 137A is provided internal to conductor 134A.

Figure 13:
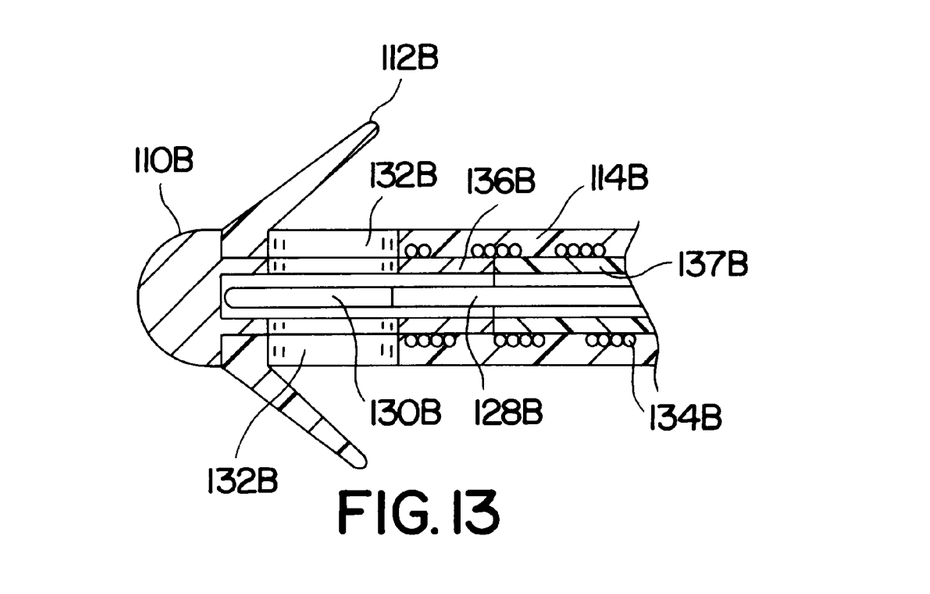
FIG. 13 is a cross-sectional view of a lead according to the second group of embodiments of the present invention employing a guidewire carrying an ultrasound transducer.

FIG. 13 is a sectional view through the distal portion of a fifth embodiment of a lead according to the second group of embodiments in the present invention, employing a guidewire carrying an ultrasound transducer. An electrode 110B is mounted to the distal end of the insulated lead body 114B, which also carries pliant times 112B. The distal portion of electrode 110B is provided with lateral openings 132B, exposing the ultrasound transducer 130B to body fluid. Openings 132B extend through shank 136A of the electrode and through lead body 114B. The diameter of Electrode shank 136A is coupled to a connector pin at the proximal end of the lead by means of coiled conductor 134B which may be welded or otherwise attached to electrode shank 136A. An optional insulative sleeve 137B is provided internal to conductor 134B.

Figure 14:
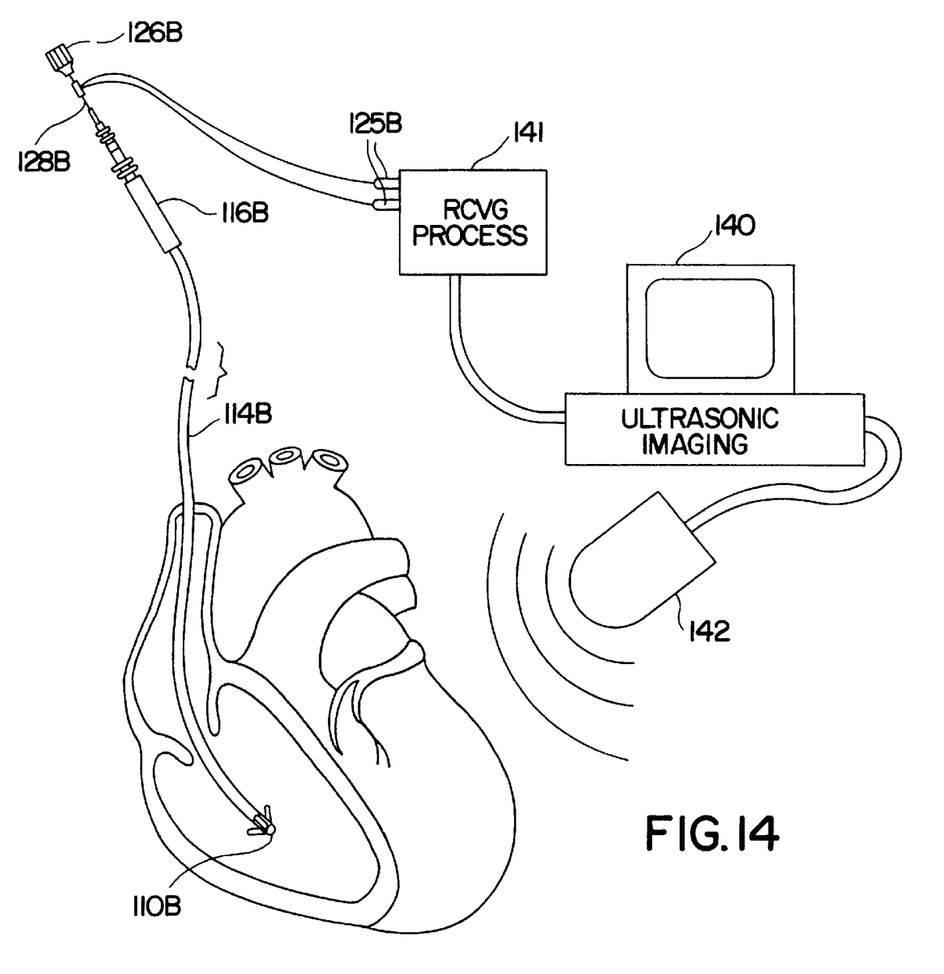
FIG. 14 illustrates the use of a lead according to the first group of embodiments of the present invention, using a stylet carrying an ultrasound transducer.

FIG. 14 illustrates the method of use of a leads according to the embodiment of the present invention illustrated in FIG. 13, employing a stylet carrying an ultrasound transducer. The lead body 114B is advanced through the vascular system into the ventricle by means of stylet 128B, shown extending from connector assembly 116B, using stylet knob 126B. When illuminated by ultrasound scanner 142, the transducer 130B within electrode 110B transmits signals to processing circuitry 141, corresponding to the processing circuitry in the above-cited Vilkomerson et al patent, and the location of the ultrasound transducer 130B is indicated relative to the ultrasound scan, by means of the display portion of the ultrasound imaging system 140. When employing a lead according to the embodiment illustrated in FIG. 12 having an ultrasound transducer on a guidewire, the lead is positioned as illustrated in FIG. 9, substituting the imaging system and processing circuitry of FIG. 14.

Figure 15:
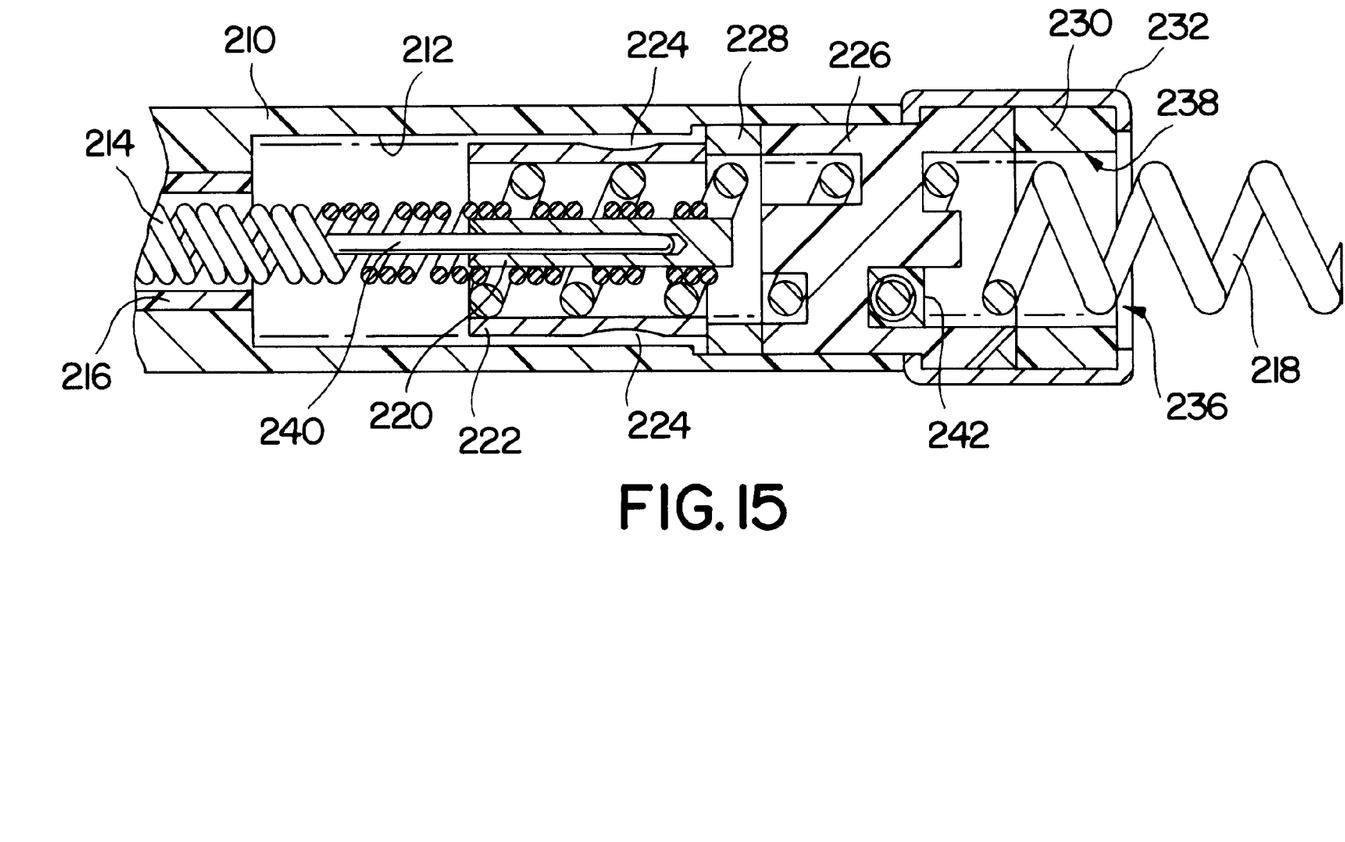
FIG. 15 is a cross-sectional view of an alternative embodiment of a lead according to the first group of embodiments, employing a vibrating stylet.

FIG. 15 is a cross-sectional view through the distal portion of an endocardial screw-in lead adapted for use in conjunction with a vibrating stylet. The lead is provided at its distal end with an electrode head member 210 fabricated of biocompatible plastic and having an internal lumen 212 in which advanceable metal fixation helix/electrode 218 is rotatably mounted. Helix 218 is coupled to coiled conductor 214 by means of a crimp sleeve 224 mounted around the exterior of the proximal portion of the helix 218 and a crimp core 220, mounted interior to the distal end of coiled conductor 214. Crimps 224 compress helix 218 around coiled conductor 214, providing mechanical and electrical interconnection. A radiopaque marker 228 is provided, which may be used in conjunction with fluoroscopy to determine the degree of advancement of fixation helix 218. If, however, fluoroscopy is not available, vibrating stylet 240 may be inserted into the central lumen of crimp core 220, coupling the vibrating stylet to the helix 218, allowing for visualization of the distal end of the lead using an ultrasound scanner, as discussed above in conjunction with other leads according to the first set of embodiments of the present invention. The distal end of the lead is provided with a metallic cap member 232 which serves to hold monolithic controlled release device 230 to the distal end of helical guide member 226. Monolithic controlled release device 230 may deliver a steroid such as sodium dexamethasone phosphate which exits through the distal opening 236 in the end cap member 232, and into contact with body tissue adjacent helix 218.

Rotation of coiled conductor 214 causes advancement and retraction of helix 218, due to its cooperation with helical guide member 226 which may also be molded of biocompatible plastic. A fluid seal 242 may be provided, sealing the lead against fluid entry around helix 218. If so provided, it is desirable that the seal does not engage the helix too tightly. For example, a 0.003 inch clearance between the seal and the helix should allow efficient transmission of vibrations from stylet 240 to the portion of helix 218 which is located within body fluids. In alternative embodiments, a fluid seal may instead be provided across the distal end of the lead. In such alternative embodiments, a slight clearance between the helix and the seal remains desirable in order to allow a sufficient vibration of helix 218 to allow ultrasound visualization. In alternative embodiments of screw-in leads adapted for use in conjunction with vibrating stylets, the vibrating stylet may be substituted for a screw driver type stylet as in U.S. Pat. No. 4,217,913 issued to Dutcher and incorporated herein by reference in its entirety or may be substituted for the stylet employed to push the helix out the distal end of the lead in conjunction with the lead illustrated in U.S. Pat. No. 4,570,642 issued to Kane et al., also incorporated herein by reference in its entirety.

In conjunction with the above specification, we claim:

1. A system for implanting a medical electrical lead, comprising:

a stylet;

a medical lead having lead body with a longitudinal lumen and an aperture located in a distal portion of the lead body, open to the lumen, the stylet insertable in the lumen of the lead body, the aperture configured to prevent passage of the stylet therethrough;

an electrode mounted to the distal portion of the lead body; and an ultrasonic vibrator mountable to the stylet.

2. A system for implanting a medical lead, comprising:

a guidewire;

a medical lead having lead body with a longitudinal lumen and an aperture located in a distal portion of the lead body, open to the lumen, the guidewire insertable in the lumen of the lead body, the aperture configured to allow passage of the guidewire therethrough;

an electrode mounted to the distal portion of the lead body; and an ultrasonic vibrator mountable to the guidewire.

3. A system for implanting a medical electrical lead, comprising:

a stylet having an ultrasound transducer located on a distal portion thereof;

a medical lead having lead body with a longitudinal lumen and an aperture located in a distal portion of the lead body, open to the lumen, the stylet insertable in the lumen of the lead body such that the transducer on the stylet is located adjacent the aperture in the lead body, the aperture configured to prevent passage of the stylet therethrough; and an electrode mounted to the distal portion of the lead body.

4. A system for implanting a medical lead, comprising:

a guidewire having an ultrasound transducer located on a distal portion thereof;

a medical lead having lead body with a longitudinal lumen and an aperture located in a distal portion of the lead body, open to the lumen, the guidewire insertable in the lumen of the lead body, the aperture configured to allow passage of the guidewire therethrough; and an electrode mounted to the distal portion of the lead body.

5. A system for implanting a medical electrical lead, comprising:

a stylet;

a medical lead having lead body with a longitudinal lumen the stylet insertable in the lumen of the lead body;

an electrode mounted to the distal portion of the lead body, having means for mechanically engaging a distal portion of the stylet; and an ultrasonic vibrator mountable to the stylet.

* * * * *